(12) United States Patent
Chen

(10) Patent No.: US 11,874,209 B2
(45) Date of Patent: Jan. 16, 2024

(54) ISOLATION DEVICE AND ISOLATION METHOD FOR ISOLATING TARGET PARTICLES FROM LIQUID SAMPLES

(71) Applicant: Shenzhen Huixin Life Technologies Co., Ltd, Shenzhen (CN)

(72) Inventor: Yuchao Chen, Rodeo, CA (US)

(73) Assignee: Shenzhen Huixin Life Technologies Co., Ltd, Shenzhen (CN)

( * ) Notice: Subject to any disclaimer, the term of this patent is extended or adjusted under 35 U.S.C. 154(b) by 79 days.

(21) Appl. No.: 17/576,654

(22) Filed: Jan. 14, 2022

(65) Prior Publication Data
US 2022/0136938 A1 May 5, 2022

Related U.S. Application Data

(63) Continuation-in-part of application No. PCT/CN2019/096425, filed on Jul. 17, 2019.

(51) Int. Cl.
| | |
|---|---|
| G01N 33/68 | (2006.01) |
| G01N 21/33 | (2006.01) |
| G01N 21/64 | (2006.01) |
| G01N 33/52 | (2006.01) |
| C07C 309/65 | (2006.01) |
| C07C 309/73 | (2006.01) |

(Continued)

(52) U.S. Cl.
CPC ............. G01N 1/34 (2013.01); G01N 1/4005 (2013.01); G01N 2001/4016 (2013.01)

(58) Field of Classification Search
CPC .................. G01N 1/34; G01N 1/4005; G01N 2001/4016; G01N 1/4077; G01N 2001/4088; G01N 35/00; B01L 2200/0668; B01L 2300/0681; B01L 2400/049; B01L 3/502; C12M 47/02; C12M 47/10; C12M 47/04; C12M 41/48
See application file for complete search history.

(56) References Cited

U.S. PATENT DOCUMENTS

2018/0200677 A1* 7/2018 Lee .................. B01L 3/502753
2019/0160432 A1 5/2019 Chen

FOREIGN PATENT DOCUMENTS

| CN | 108126522 | * | 6/2008 |
| CN | 208297542 U | | 12/2018 |

(Continued)

*Primary Examiner* — Jennifer Wecker
*Assistant Examiner* — Oyeleye Alexander Alabi
(74) *Attorney, Agent, or Firm* — ScienBiziP, P.C.

(57) ABSTRACT

An isolation device for isolation of target particles from a plurality of liquid samples includes a plurality of isolation chips and a vacuum system. Each of the plurality of isolation chips includes a sample reservoir, and a first outlet and a second outlet disposed at opposite sides of the sample reservoir. The vacuum system includes a first vacuum pump connected to the first outlet of each of the plurality of isolation chips and a second vacuum pump connected to the second outlet of each of the plurality of isolation chips. The first vacuum pump generates a negative pressure in each of the plurality of isolation chips through a corresponding first outlet. The second vacuum pump generates a negative pressure in each of the plurality of isolation chips through a corresponding second outlet. The target particles are isolated from each of the plurality of liquid samples in a corresponding sample reservoir.

6 Claims, 8 Drawing Sheets

(51) Int. Cl.
    *A01N 1/02*     (2006.01)
    *G01N 1/40*     (2006.01)
    *G01N 33/543*     (2006.01)
    *G01N 33/532*     (2006.01)
    *G01N 33/569*     (2006.01)
    *G01N 35/00*     (2006.01)
    *G01M 3/02*     (2006.01)
    *G01N 35/10*     (2006.01)
    *G01N 1/34*     (2006.01)

(56) References Cited

FOREIGN PATENT DOCUMENTS

| | | |
|---|---|---|
| CN | 109439533 A | 3/2019 |
| EP | 1637886 A1 | 3/2006 |

\* cited by examiner

ISOLATION DEVICE AND ISOLATION METHOD FOR ISOLATING TARGET PARTICLES FROM LIQUID SAMPLES

FIELD

The subject matter herein generally relates to biotechnology, and more particularly, to an isolation device and an isolation method for isolating target particles from liquid samples.

BACKGROUND

Exosomes are small vesicles with a structure of double phospholipid membranes having a size of 30 to 150 nm, which are continuously secreted by living cells. As a carrier in the intercellular communication, exosomes carry specific components, such as proteins, nucleic acids, and metabolic small molecules, from mother cells. A large number of studies have shown that exosomes are involved in a variety of events in tumor development, including immune escape, angiogenesis, tumor metastasis, and tumor drug resistance. Exosomes can be continuously released by cancer cells and then enter a patient's blood circulation system. The double phospholipid membranes can effectively protect the carried proteins and nucleic acids. Exosomes widely and stably exist in a variety of clinical samples, including blood, urine, ascites, tissue fluid, tears, saliva, and cerebrospinal fluid. The number of exosomes in blood and urine is large, and clinical sampling is easy. Therefore, exosomes are considered to be the key research objects in the field of in vitro diagnostic research and tumor clinical detection. Exosomes are expected to play a great clinical value in early tumor diagnosis, evaluation of tumor metastasis and recurrence, evaluation of tumor heterogeneity, dynamic detection of tumor occurrence, development and curative effect, detection of drug-resistant mutations, and personalized drugs.

At present, the main obstacle to the clinical application of exosomes is the lack of a standard method that extract high-purity exosomes in a rapid, stable, and efficient way. There are a variety of purification technologies of exosomes on the market, including ultracentrifugation, size exclusion chromatography, immunoaffinity capture based on magnetic beads, precipitation based on polyethylene glycol, ultrafiltration, and microfluidic technologies. However, the above-mentioned purification methods have the following disadvantages: 1) low recovery rate, 2) low purity, 3) poor integrity of isolated exosomes, 4) poor reproducibility, 5) possible introduction of unwanted impurities, 6) need for biomarkers, 7) high time consumption, and 8) high cost. Ultracentrifugation is the most commonly used method for the purification of exosomes, but also has some limitations, such as low yield (a recovery rate being only 5% to 25%), cumbersome operation process, time-consuming (greater than 4 hours), and dependence on expensive equipment. In addition, the isolation method based on immune capture can collect exosomes with a medium or a high purity. But limited by the specificity of antibodies and cumbersome operation process, the isolation method is difficult to standardize, and is not suitable for dealing with a large number and large volume of clinical samples. Recently, the isolation method of exosomes based on microfluidic technology has also been reported, including hydrodynamic or acoustic isolation, immune capture, and dielectric electrophoresis. However, the isolation method still cannot solve the problems of low yield, complex operation process, and poor repeatability, and is difficult to achieve the consistency of results among different laboratories.

BRIEF DESCRIPTION OF THE DRAWINGS

Implementations of the present disclosure will now be described, by way of embodiments only, with reference to the attached figures.

DETAILED DESCRIPTION

Implementations of the disclosure will now be described, by way of embodiments only, with reference to the drawings. The disclosure is illustrative only, and changes may be made in the detail within the principles of the present disclosure. It will, therefore, be appreciated that the embodiments may be modified within the scope of the claims.

It should be noted that when a component is said to be "fixed" to another component, it may be directly attached to another component, or a middle component may exist therebetween. When a component is considered to be "connected" to another component, it may be directly connected to another component, or a middle component may exist therebetween. When a component is said to be "disposed on" another component, it may be directly disposed on another component, or a middle component may exist therebetween.

Unless otherwise defined, all technical terms used herein have the same meaning as commonly understood by one of ordinary skill in the art. The technical terms used herein are not to be considered as limiting the scope of the embodiments.

Figure 1:
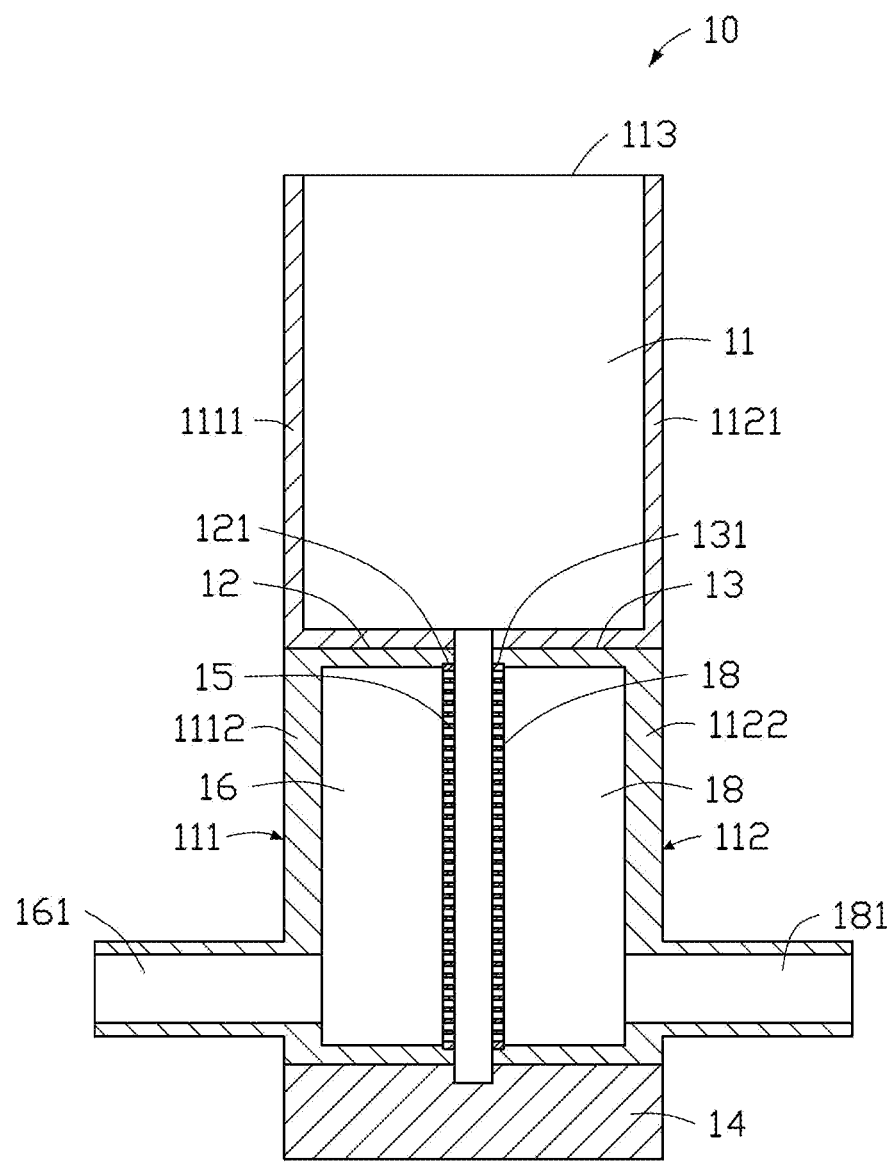
FIG. 1 is a diagrammatic view of an embodiment of an isolation chip according to the present disclosure.
Figure 2:
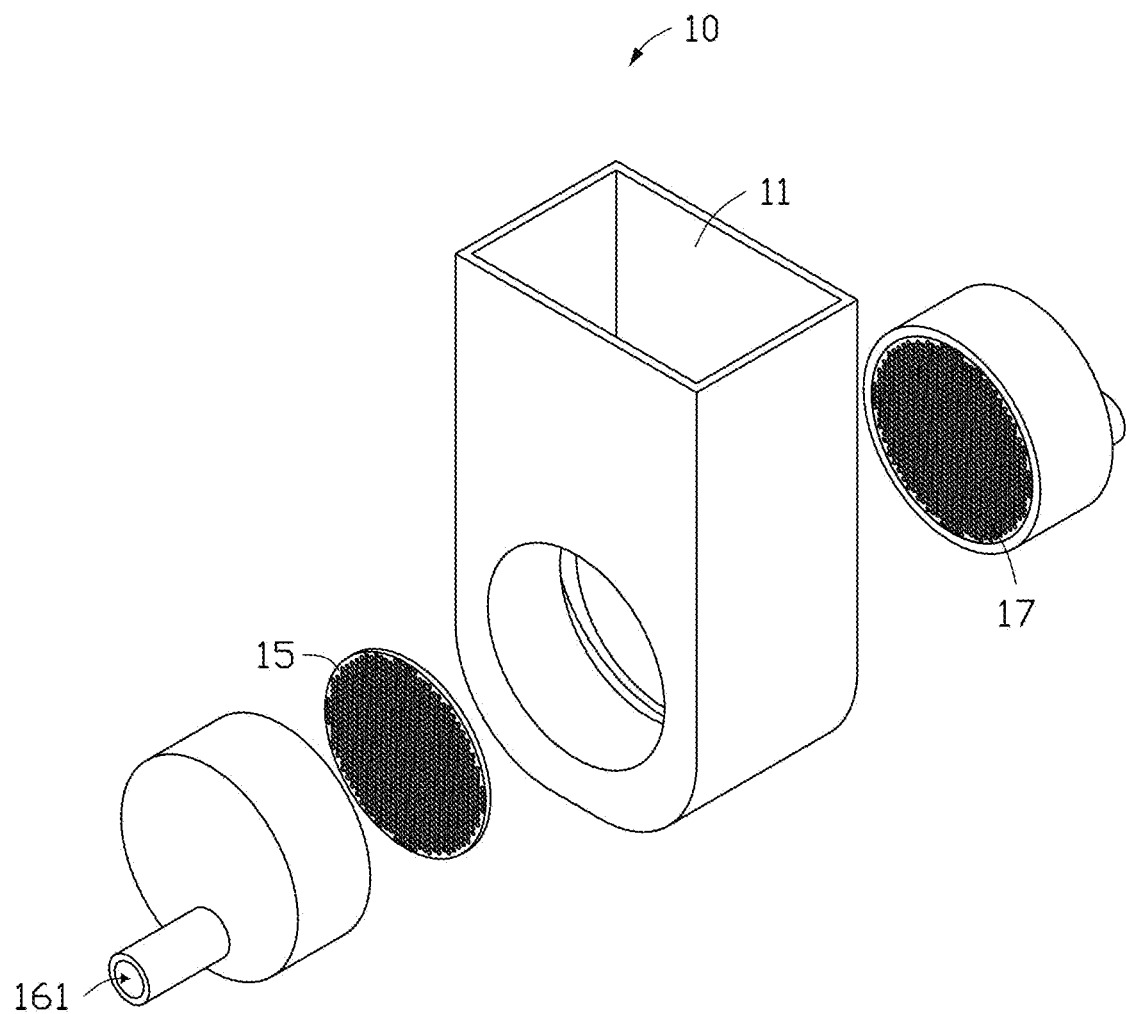
FIG. 2 is an exploded view of the isolation chip of FIG. 1.

An embodiment of an isolation chip 10 is provided, which is adapted for isolating particles of different sizes from a liquid sample. Then, target particles of a specific size can be obtained. The liquid sample can be a bioliquid such as plasma, serum, saliva, urine, and lavage. The target particles can be human plasma, serum, cerebrospinal fluid, saliva, urine, tear, emulsion, gastric juice, cell culture liquid, etc. FIG. 1 illustrates an embodiment of the isolation chip 10 according to the present disclosure. As shown in FIGS. 1 and 2, the isolation chip 10 includes a sample reservoir 11, a first chamber 16, a second chamber 18. The first chamber 16 and the second chamber 18 are disposed at opposite sides of the sample reservoir 11.

The sample reservoir 11 includes a first side cover 111 and a second side cover 112 disposed at opposite sides of the sample reservoir 11. The first side cover 111 includes a first protruding block 12, which divides the first side cover 111 into a first cover portion 1111 and a second cover portion 1112 at opposite sides of the first protruding block 12. The second side cover 112 includes a second protruding block 13 facing the first protruding block 12. The second protruding block 13 divides the second side cover 112 into a third cover portion 1121 and a fourth cover portion 1122 at opposite sides of the second protruding block 13. The first cover portion 1111, the third cover portion 1121, the first protruding block 12, and the second protruding block 13 cooperatively define the sample reservoir 11. A sample inlet 113 is disposed on a top of the sample reservoir 11. A liquid sample can be injected or extracted out through the sample inlet 113.

A chip base 14 is disposed at a bottom of the first side cover 111 and faces the first protruding block 12. A first filtration membrane 15 is disposed between the first protruding block 12 and the chip base 14. The first filtration membrane 15 faces the second cover portion 1112. The second cover portion 1112, the first filtration membrane 15, and the chip base 14 cooperatively define the first chamber 16. The first chamber 16 defines a first outlet 161, which connects the first chamber 16 to an ambient environment.

Another chip base 14 is disposed at a bottom of the second side cover 112 and faces the second protruding block 13. A second filtration membrane 17 is disposed between the second protruding block 13 and the chip base 14. The second filtration membrane 17 faces the fourth cover portion 1122. The fourth cover portion 1122, the second filtration membrane 17, and the chip base 14 cooperatively define the second chamber 18. The second chamber 18 defines a second outlet 181, which connects the second chamber 18 to the ambient environment.

In at least one embodiment, a gap (not labeled in the drawings) is formed between the first protruding block 12 and the second protruding block 13, so that the liquid sample in the sample reservoir 11 can flow out of the sample reservoir 11, and then enter the first chamber 16 or the second chamber 18 through the first filtration membrane 15 or the second filtration membrane 17. In detail, a side of the first protruding block 12 facing the chip base 14 defines a first slot 121. The chip base 14 defines a second slot (not labeled) at a corresponding position. The first filtration membrane 15 is fixedly latched between the first slot 121 and the second slot. Similarly, a side of the second protruding block 13 facing the chip base 14 defines a third slot 131. The chip base 14 defines a fourth slot (not labeled) at a corresponding position. The second filtration membrane 17 is fixedly latched between the third slot 131 and the fourth slot.

The isolation chip 10 has a symmetrical structure. It should be noted that the isolation chip 10 may also be asymmetrical or any other structure that can perform the function of the present disclosure.

In use, the liquid sample is added to the sample reservoir 11. Each of the first outlet 161 and the second outlet 181 is connected to a vacuum system 30 (shown in FIG. 4). When the vacuum system 30 generates a negative pressure in the first chamber 16 through the first outlet 161, compositions in the liquid sample that are smaller than the pores of the first filtration membrane 15 can enter the first chamber 16 through the first filtration membrane 15. When the vacuum system 30 generates a negative pressure in the second chamber 18 through the second outlet 181, compositions in the liquid sample that are smaller than the pores of the second filtration membrane 17 can enter the second chamber 18 through the second filtration membrane 17. In an embodiment, the vacuum system 30 includes two vacuum pumps, one connects to the first outlet 161 and the other one connects to the second outlet 181. The two vacuum pumps alternately provide negative pressure. Since negative pressure is alternately applied in the first chamber 16 and the second chamber 18, the compositions in the liquid sample can alternately flow through the first filtration membrane 15 and the second filtration membrane 17. Thus, target particles that are larger than the pores of the first filtration membrane 15 and the second filtration membrane 17 remain in the sample reservoir 11. Furthermore, some of the target particles that are absorbed on the first filtration membrane 15 and the second filtration membrane 17 can be flushed out under the negative pressure, thereby avoiding clogging of the first filtration membrane 15 and the second filtration membrane 17.

Figure 3:
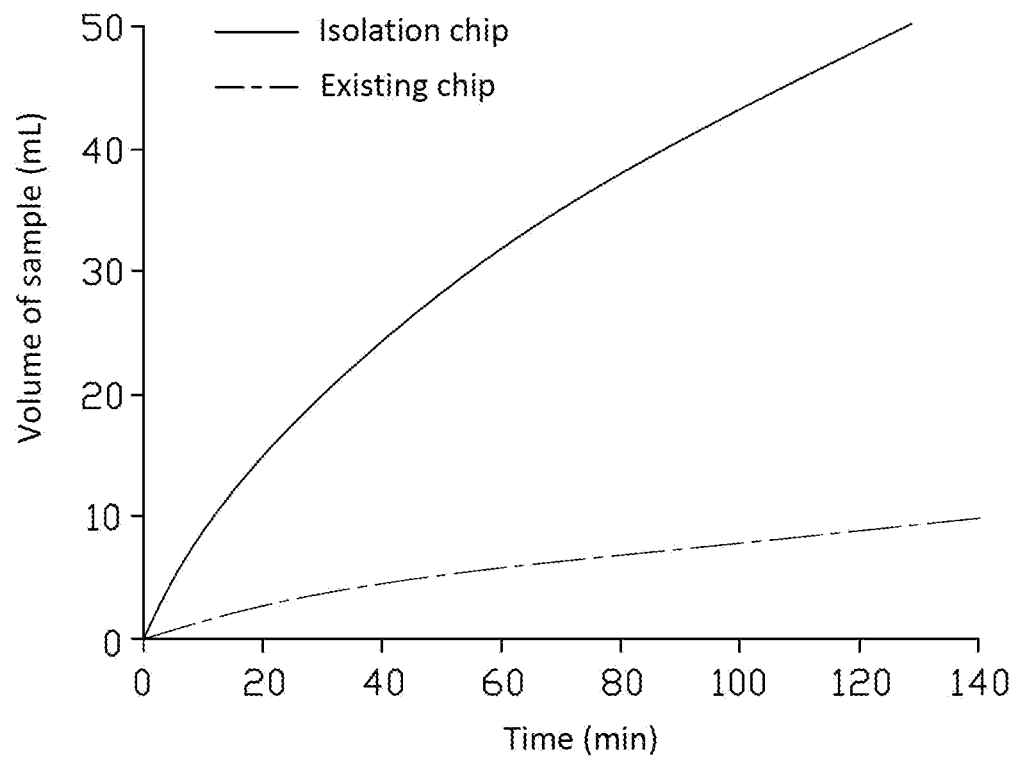
FIG. 3 is a diagram showing speeds of isolation of exosomes by the isolation chip of FIG. 1 and an existing chip.

Exchange filtration and membrane vibration, generated under the action of an alternating negative pressure, allow exosomes to be suspended during an isolation process to avoid clogging of membranes. Compared with the existing filtration membranes, experimental results, which are shown in FIG. 3, indicate that the isolation chip 10 can purify each of 20 mL urine sample and 20 mL cell culture liquid sample in 30 minutes, far more than the existing ultrafiltration method (3 mL).

The sample reservoir 11, the first filtration membrane 15, and the second filtration membrane 17 of the isolation chip 10 can mainly be made of plastic, glass, metal, or a composite material. In an embodiment, the sample reservoir 11, the first filtration membrane 15, and the second filtration membrane 17 of the isolation chip 10 can mainly be made of polyethylene imine (PEI), polymethyl methacrylate (PMMA), or another transparent material. Processing methods of the isolation chip 10 include, but are not limited to, processing molding and injection molding. The first filtration membrane 15 and the second filtration membrane 17 may be made of a same material or different materials. The first filtration membrane 15 and the second filtration membrane 17 may have a same average pore size and/or a same pore size distribution, or may have different average pore sizes and/or different pore size distributions. The first filtration membrane 15 (or the second filtration membrane 17) may be made of a single material or a combination of multiple materials. The first filtration membrane 15 and the second filtration membrane 17 may have porous materials, including but not limited to porous ceramic materials, porous plastic materials, and porous metal materials. Specifically, each of the first filtration membrane 15 and the second filtration membrane 17 may be made of anodic aluminum oxide (AAO), polycarbonate, acetate fibers, polyethylene, polypropylene, polystyrene, and any combination thereof. More specifically, both the first filtration membrane 15 and the second filtration membrane 17 are made of anodic aluminum oxide that have a high porosity and an average pore size.

The pore sizes of the first filtration membrane 15 and the second filtration membrane 17 can be varied according to the type of liquid samples and the type of target particles. In an embodiment, the pore sizes of the first filtration membrane 15 and the second filtration membrane 17 are 20 nm, which are slightly less than the sizes of exosomes (30~150 nm). Thus, exosomes can be isolated and purified from a cell culture sample that have passed a filtration membrane with a pore size of 200 nm.

Figure 4:
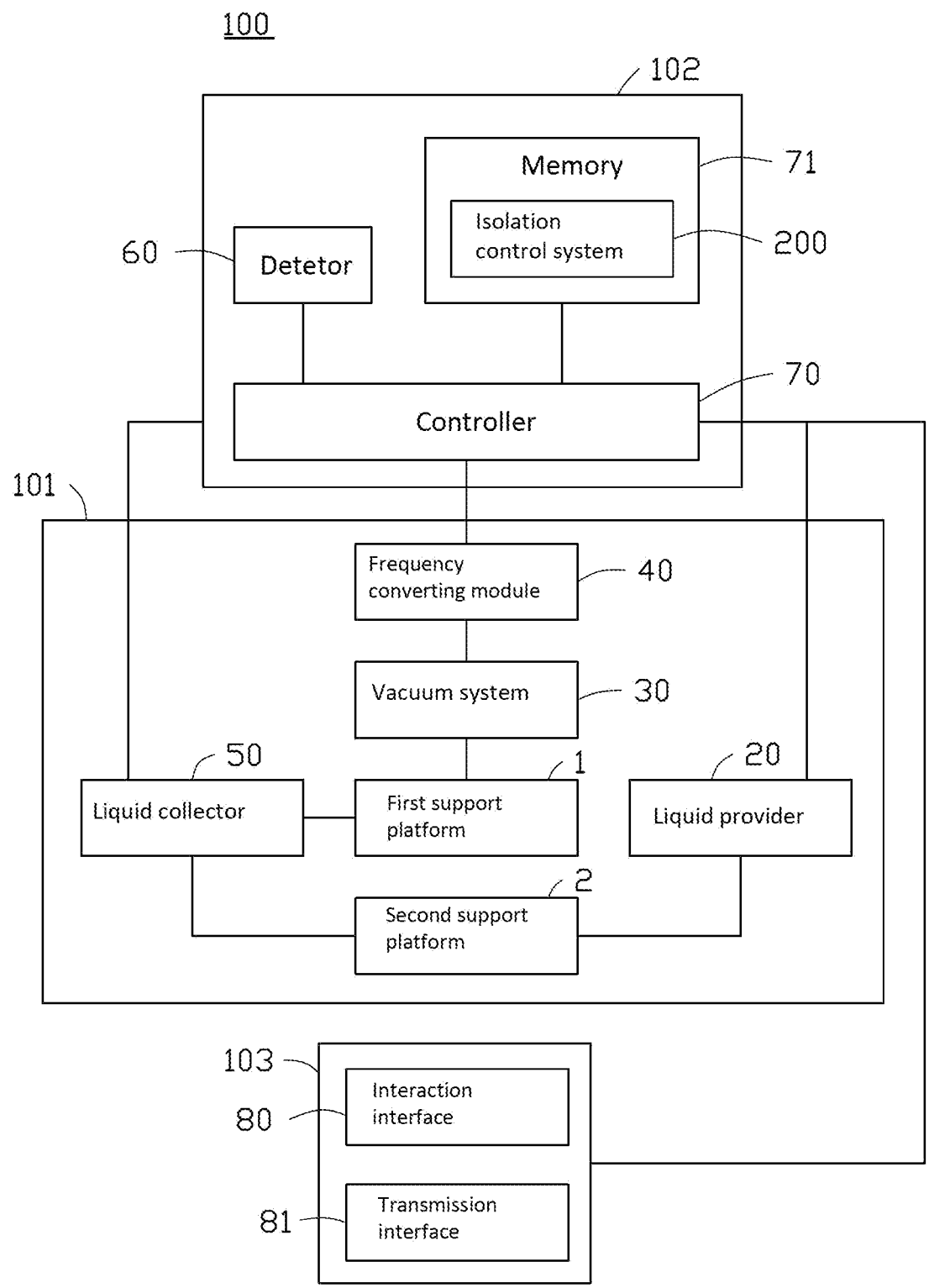
FIG. 4 is a block diagram of an embodiment of an isolation device according to the present disclosure.

An embodiment of an isolation device 100 is further provided according to the present disclosure. FIG. 4 illustrates the isolation device 100 including a main module 101, an auxiliary module 102, and an interaction module 103.

The main module 101 is configured to isolate and purify target particles from a number of liquid samples, thereby improving purify efficiency. The main module 101 includes a first support platform 1, a second support platform 2, a liquid provider 20, the vacuum system 30, a frequency converting module 40, and a liquid collector 50.

Figure 7:
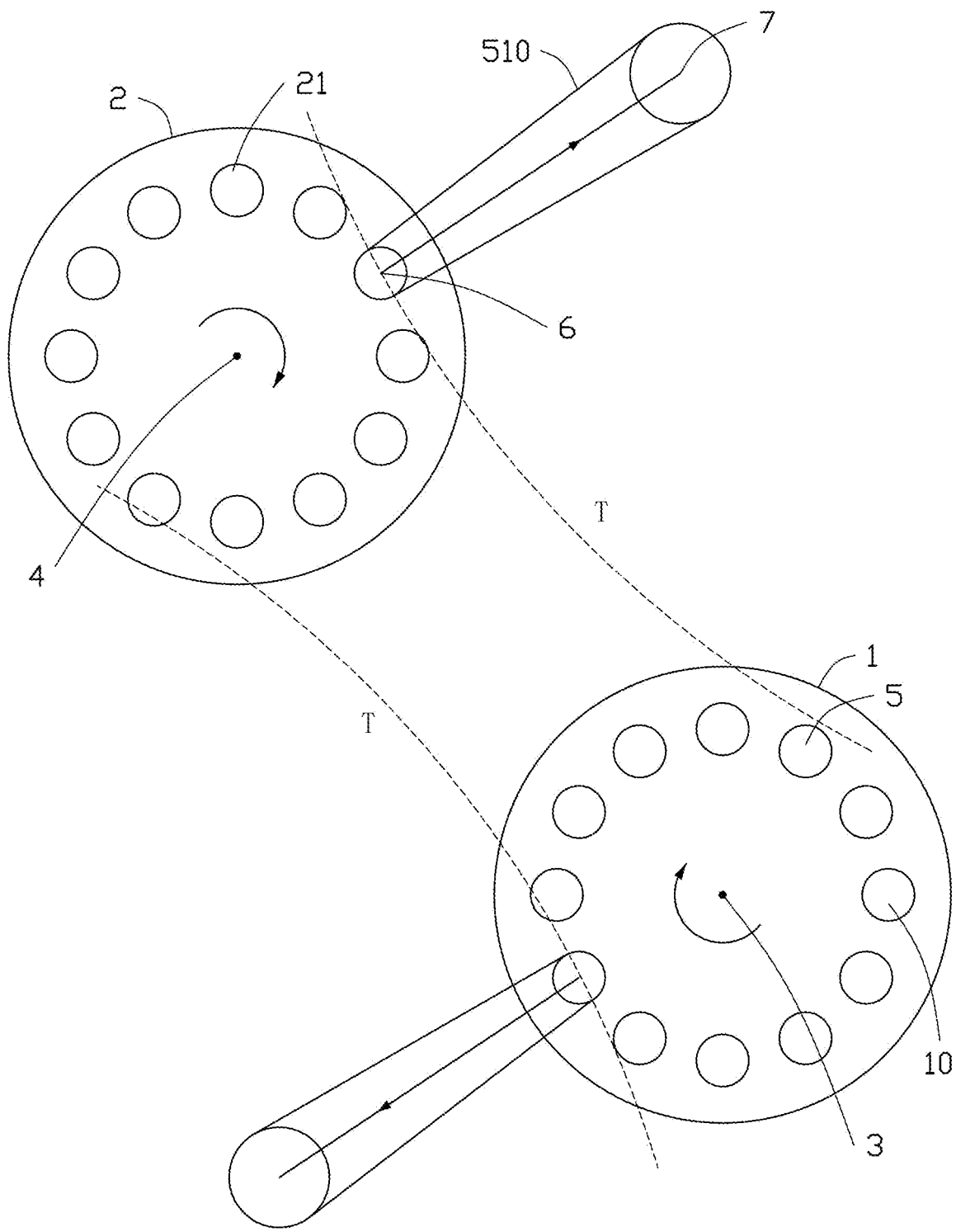
FIG. 7 is a diagrammatic view showing a working principle of a sampling member of the isolation device of FIG. 4.

FIG. 7 shows that the first support platform 1 supports a number of the isolation chips 10 as described above. In an embodiment, the number of the isolation chips 10 on the first support platform 1 is 12. The first support platform 1 can be rotated by a driver (such as a motor, not shown) about a first shaft 3, along a clockwise or counterclockwise direction for example, to rotate each isolation chip 10 on the first support platform 1, so that the isolation chips 10 are successively moved to a first preset position 5. The first preset position 5 is a sampling position. The isolation chips 10 are arranged on the first support platform 1 around the first shaft 3 of the first support platform 1. It is understood that the number of the isolation chips 10 on the first support platform 1 can be increased or decreased as required.

The second support platform 2 comprises a plurality of containers 21. In an embodiment, the number of the containers 21 is 12, which is the same as the number of the isolation chips 10. The second support platform 2 can be rotated about a second shaft 4 by a driver (such as a motor, not shown), along the clockwise or counterclockwise direction, to rotate each container 21 on the second support platform 2, so that the containers 21 are successively moved to a second preset position 6. The containers 21 are arranged on the second support platform 2 around the second shaft 4 of the second support platform 2.

Figure 5A:
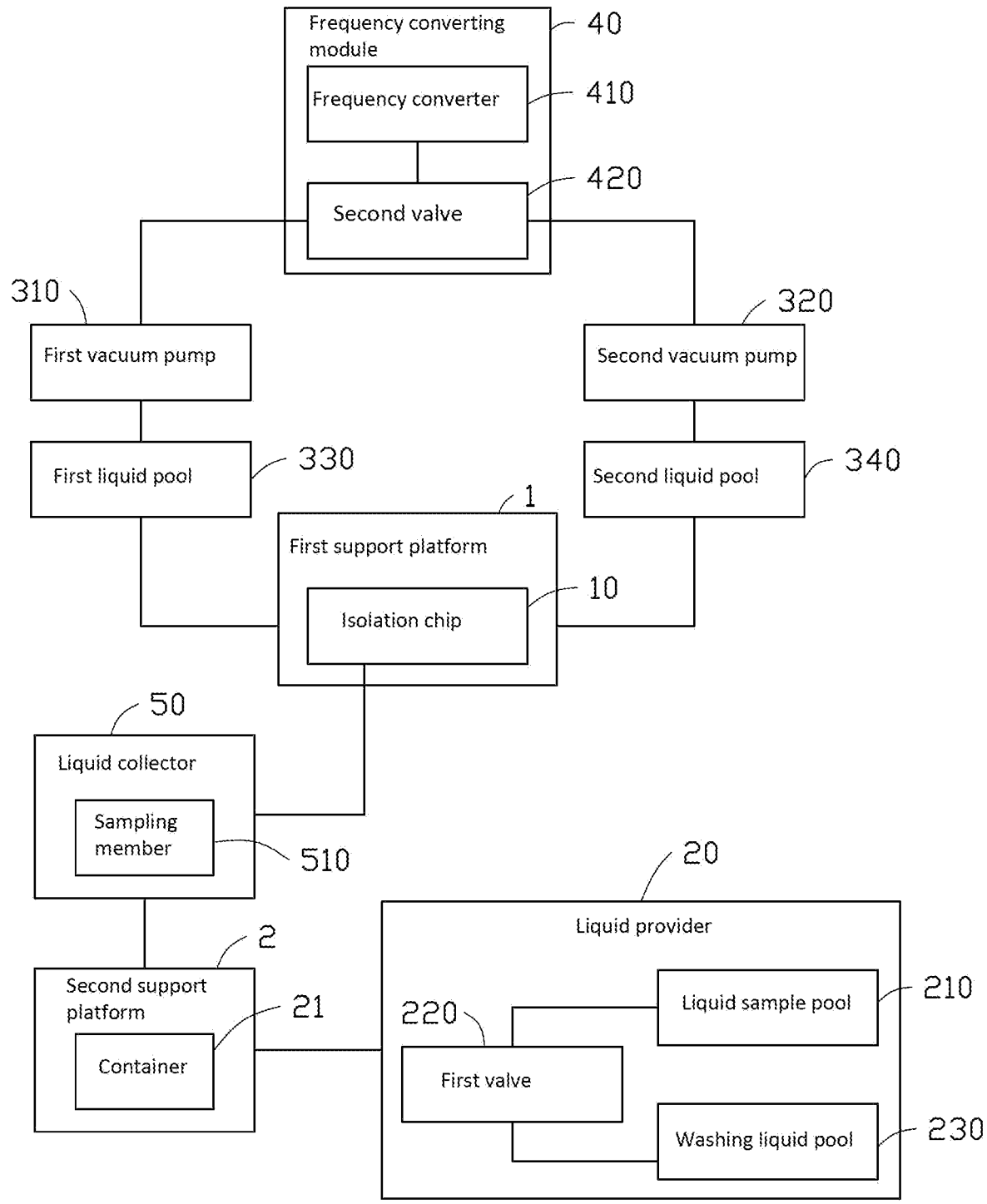
FIG. 5A is a diagrammatic view of a liquid path of the isolation device of FIG. 4.

Referring to FIG. 5A, the liquid provider 20 includes a liquid sample pool 210, a first valve 220, and a washing liquid pool 230. The liquid sample pool 210 receives a same liquid sample or different liquid samples. The washing liquid pool 230 receives a washing liquid. The first valve 220 can control the liquid sample(s) in the liquid sample pool 210 and the washing liquid in the washing liquid pool 230 to be added to the containers 21.

The liquid collector 50 includes at least one sampling member 510 that can be rotated about a third shaft 7 to form a sampling trajectory T. The first preset position 5 and the second preset position 6 are disposed on the sampling trajectory T. Each sampling member 510 is used to collect the liquid sample or the washing liquid in the container 21 at the second preset position 6, and to inject the collected liquid sample or washing liquid into the isolation chip 10 at the first preset position 5, so that the isolation chip 10 can isolate and wash the target particles. In an embodiment, each sampling member 510 is a sampling needle, and two sampling needles are included. One sampling member 510 is on one side of a line connecting the first support platform 1 and the second support platform 2, and the other sampling member 510 is on the other side of the line connecting the first support platform 1 and the second support platform 2. Each sampling member 510 corresponds to one sampling trajectory T. Two first preset positions 5 and two second preset positions 6 are included. One of the first preset positions 5 and the corresponding second preset position 6 are located on the sampling trajectory T of one sampling member 510, and the other first preset position 5 and the corresponding second preset position 6 are located on the sampling trajectory T of the other sampling member 510. The two sampling members 510 can work simultaneously or independently. The liquid provider 20 may also include a driving component, such as a power pump or an air pump, to driving the liquid to flow.

The vacuum system 30 alternately generates a negative pressure in the first chamber 16 and the second chamber 18 of each isolation chip 10 on the first support platform 1. The vacuum system 30 can include two independent vacuum units or a single vacuum system. The vacuum system 30 may also include equipment such as micro-vacuum pumps or micro-suction pumps. It is understood that the vacuum system 30 and each isolation chip 10 can be connected by an air-tight pipe. In an embodiment, the vacuum system 30 includes a first vacuum pump 310 and a second vacuum pump 320. The isolation chips 10 are connected in parallel between the first vacuum pump 310 and the second vacuum pump 320. That is, the first vacuum pump 310 is connected to the first outlet 161 of each isolation chip 10. The second vacuum pump 320 is connected to the second outlet 181 of each isolation chip 10.

The frequency converting module 40 is electrically connected to the vacuum system 30, and provides an electric power to the vacuum system 30, so that the negative pressure can be alternately generated in the first chamber 16 and the second chamber 18. Since the isolation chips 10 are connected in parallel, the negative pressure of the same intensity can be alternately generated in each isolation chip 10 at the same time. In other embodiments, when the number of the isolation chips 10 simultaneously working on the first support platform 1 is large (more than 6), the isolation chips 10 can be divided into two or more groups, which are connected to a number of the vacuum systems 30, so as to ensure stable negative pressure without attenuation.

Figure 6:
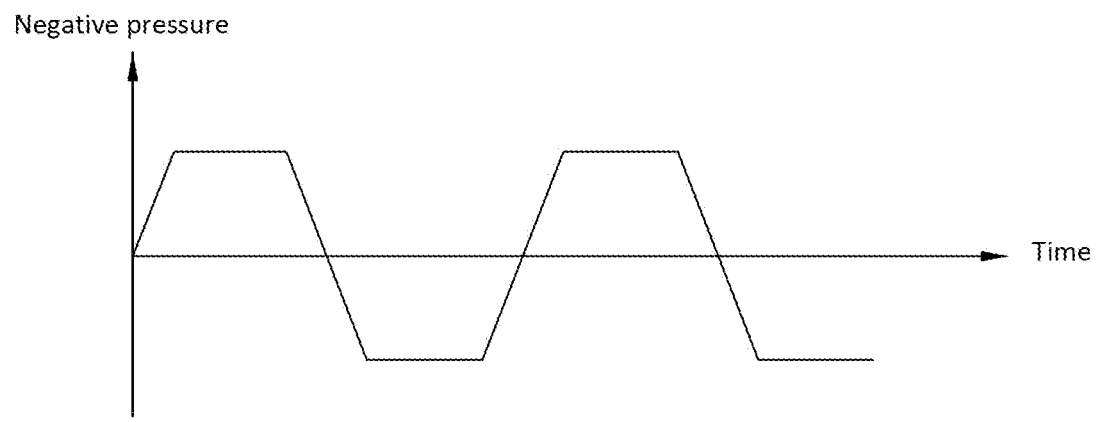
FIG. 6 is a diagram of an embodiment of negative pressure applied to the isolation chip.

In an embodiment, the frequency converting module 40 includes a frequency converter 410 and a second valve 420 connected to the frequency converter 410. The second valve 420 can be a liquid path converter, including but not limited to an electromagnetic valve or a rotary valve. The second valve 420 is alternately switched to connect one of the first vacuum pump 310 and the second vacuum pump 320, to cause the vacuum system 30 to alternately apply the negative pressure in the first chamber 16 and the second chamber 18. That is, when the second valve 420 connects to the first vacuum pump 310, the frequency converter 410 controls the first vacuum pump 310 to operate, which generate the negative pressure in each first chamber 16 by evacuating through each first outlet 161. Thus, the compositions in each sample reservoir 11 that are smaller than the pores of the corresponding first filtration membrane 15 can pass through the corresponding first filtration membrane 15 under the negative pressure and enter the corresponding first chamber 16. At the same time, the back flow of the liquid sample in each sample reservoir 11 adjacent to the corresponding second filtration membrane 17 prevents any composition from accumulating in the pores of the corresponding second filtration membrane 17. Thus, clogging of the filtration membrane can be avoided. Then, the frequency converter 410 controls the first vacuum pump 310 to stop operating, and the second valve 420 is switched to connect to the second vacuum pump 320. The frequency converter 410 controls the second vacuum pump 320 to operate, which generates the negative pressure in each second chamber 18 by evacuating through each second outlet 181. Thus, the compositions in each sample reservoir 11 that are smaller than the pores of the corresponding second filtration membrane 17 can pass through the corresponding second filtration membrane 17 under the negative pressure and enter the corresponding second chamber 18. At the same time, the back flow of the liquid sample in each sample reservoir 11 adjacent to the corresponding first filtration membrane 15 prevents any composition from accumulating in the pores of the corresponding first filtration membrane 15. Thus, clogging of the filtration membrane can be avoided. Then, the frequency converter 410 controls the second vacuum pump 320 to stop operating. The above-described procedures are repeated until complete isolation is achieved. Referring to FIG. 6, in an embodiment, the negative pressure alternating in each first chamber 16 and each second chamber 18 is caused by trapezoidal wave shaped pulse signals. The trapezoidal wave shaped pulse signals have an amplitude of −10 kpa to 80 kpa. In other embodiments, the trapezoidal wave shaped pulse signals may also be replaced by a periodic sinusoidal or rectangular signal. In other embodiments, since a plasma sample may have a large amount of proteins, to further avoid clogging of the filtration membrane, a positive pressure can also be applied in one of the first chamber 16 or the second chamber 18 when applying the negative pressure in another one of the first chamber 16 or the second chamber 18, thereby reinforcing the back flow adjacent to the filtration membrane. In actual use, the amplitude, the period, and the total time durations of the negative pressure can be varied according to the type of liquid samples, to obtain a best effect of back flow adjacent to the filtration membrane. Under the action of alternating negative pressure, impurities of smaller size in a liquid sample, including but not limited to nucleic acid molecules (RNA, DNA), lipoproteins, lipids, proteins, and peptide chains, can be sucked out of the corresponding first outlet 161 and the corresponding second outlet 181 respectively through the corresponding first filtration membrane 15 and the corresponding second filtration membrane 17. The exosomes of larger size remain in the corresponding sample reservoir 11. Finally, a concentrated exosome sample with high purity is obtained from each sample reservoir 11.

Furthermore, referring to FIG. 5A, the main module 101 further includes a number of first liquid pools 330 and a number of second liquid pools 340. Each first liquid pool 330 is connected between the first vacuum pump 310 and the first outlet 161 of one corresponding isolation chip 10, and communicates with the first vacuum pump 310 and the first chamber 16 of the isolation chip 10. Each second liquid pool 340 is connected between the second vacuum pump 320 and the second outlet 181 of one corresponding isolation chip 10, and communicates with the second vacuum pump 320 and the second chamber 18 of the isolation chip 10. The first liquid pool 330 and the second liquid pool 340 prevent the liquid sample from flowing into the first vacuum pump 310 and the second vacuum pump 320. Each first liquid pool 330 or each second liquid pool 340 can be used as a safety bottle to prevent the liquid sample in the corresponding isolation chip 10 from flowing into the vacuum pump, or used as a waste liquid bottle to collect liquid or washing liquid remaining in each isolation chip 10 after the isolation.

The auxiliary module 102 can ensure that the isolation device 100 operates normally and efficiently. The auxiliary module 102 includes a detector 60 and a controller 70.

The detector 60 detects a liquid level of the liquid sample in the sample reservoir 11.

The controller 70 is electrically connected to the detector 60 and the frequency converting module 40. The controller 70 obtains the detected liquid level, and determines whether the liquid sample or the washing liquid needs to be further added or whether the isolation of the liquid sample is finished according to the obtained liquid level and a preset amount of the liquid sample. When the isolation of the liquid sample is finished, the controller 70 controls the frequency converting module 40 to stop generating the negative pressure in the first chamber 16 and the second chamber 18. The controller 70 can be a collection of logical relationships embedded in hardware or firmware, or a series of programs written in a programming language and stored in memory or other firmware. In an embodiment, the controller 70 controls the frequency converting module 40 to generate the negative pressure in the first chamber 16 and the second chamber 18 according to preset pressure data.

The interaction module 103 allows the target particles isolation from the liquid sample to meet actual need, so that the isolation device 100 is maneuverable. The interaction module 103 includes an interaction interface 80 for a user to input data related to the isolation processes through an input unit (for example, a touch panel, a keyboard, or a mouse) of the isolation device 100. That is, the user can preset the data related to the isolation processes through the interaction interface 80. In an embodiment, the data related to the isolation processes includes the preset amount of the liquid sample, the preset amount of the washing liquid, and the preset pressure data. The preset pressure data includes the amplitude, the period, and the total time durations of the negative pressure. The controller 70 is further electrically connected to the interaction interface 80. Thus, the controller 70 can obtain the input data from the interaction interface 80, and control the frequency converting module 40 or the liquid provider 20 to operate accordingly.

In an embodiment, the interaction module 103 can further include a transmission interface 81 configured to connect the isolation device 100 to a peripheral device (for example, a smart phone or a USB flash disk). The isolation device 100 can transmit data related to the isolation processes to the peripheral device through the transmission interface 81. Thus, the user can review the data related to the isolation processes after sample isolation. The transmission interface 81 can be a USB interface or a wireless interface.

The isolation device 100 provided by the present disclosure can automatically isolate target particles from a liquid sample, thereby obtaining components in the sample reservoir 11 that cannot pass through a filtration membrane. At the same time, a direction of liquid flow in the sample reservoir 11 is changed by the change of negative pressure in chambers on both sides of the sample reservoir 11, which can reduce the amounts of components that adhering to the filtration membrane. Clogging of the filtration membrane in the isolation process can be avoided. The isolation device 100 is of low cost and easy to use, which reduces the workload of experimenters.

Figure 5B:
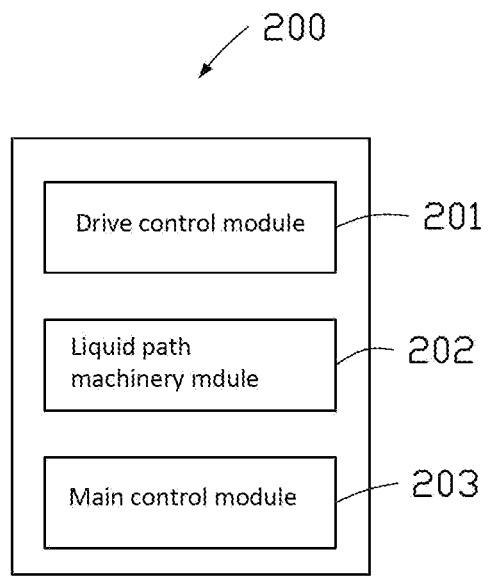
FIG. 5B is a block diagram of an isolation control system of the isolation device of FIG. 4.

An embodiment of an isolation control system 200 is further provided according to the present disclosure, which can be applied in the isolation device 100. The auxiliary module 102 of the isolation device 100 further includes a memory 71. The isolation control system 200 is stored in the memory 71. The isolation control system 200 includes a number of modules, which are a collection of software instructions executable by the controller 70 to perform the function of the isolation control system 200. Referring to FIGS. 4 and 5B, the isolation control system 200 includes a liquid path machinery module 202 and a main control module 203.

The liquid path machinery module 202 controls each sampling member 510 to provide the liquid sample and the washing liquid into the sample reservoir 11 of each isolation chip 10.

The main control module 203 controls the vacuum system 30 alternately generates the negative pressure in the first chamber 16 and the second chamber 18 of each isolation chip 10 through the frequency converting module 40. In an embodiment, the vacuum system 30 includes the first vacuum pump 310 and the second vacuum pump 320. The first vacuum pump 310 is connected to the first outlet 161 of each isolation chip 10. The second vacuum pump 320 is connected to the second outlet 181 of each isolation chip 10. The frequency converting module 40 includes the frequency converter 410 and the second valve 420 connected to the frequency converter 410. The main control module 203 controls the second valve 420 to connect to the first vacuum pump 310, so that the frequency converter 410 controls the first vacuum pump 310 to operate, which evacuates through each first outlet 161 to generate the negative pressure in the corresponding first chamber 16. The main control module 203 further controls the second valve 420 to connect to the second vacuum pump 320, so that the frequency converter 410 controls the second vacuum pump 320 to operate, which evacuates through each second outlet 181 to generate the negative pressure in the corresponding second chamber 18.

In an embodiment, the isolation device 100 further includes the detector 60. The detector 60 detects a liquid level of the liquid sample in the sample reservoir 11. The isolation control system 200 further includes a drive control module 201. The drive control module 201 obtains the detected liquid level, and determines whether the isolation of the liquid sample is finished according to the obtained liquid level and the preset amount of the liquid sample. When the isolation of the liquid sample is finished, the drive control module 201 sends a stop command to the main control module 203. The main control module 203 responds to the stop command, and controls the frequency converting module 40 to stop operating, so as to stop generating the negative pressure in the first chamber 16 and the second chamber 18 of the corresponding isolation chip 10.

In an embodiment, the drive control module 201 further obtains the preset pressure data, and sends a control command including the preset pressure data to the main control module 203. The main control module 203 responds to the control command, and controls the frequency converting module 40 to generate the negative pressure in each first chamber 16 and each second chamber 18 according to the preset pressure data. The drive control module 201 further obtains the preset amount of each liquid sample, and sends a second control command including the preset amount of each liquid sample to the liquid path machinery module 202. The liquid path machinery module 202 responds to the second control command, and controls a working duration of each sampling member 510 according to the preset amount of each liquid sample, thereby allowing the liquid sample with the preset amount to be added to the corresponding sample reservoir 11. The drive control module 201 further obtains the preset amount of the washing liquid, and sends a third control command including the preset amount of the washing liquid to the liquid path machinery module 202. The liquid path machinery module 202 responds to the third control command, and controls a working duration of each sampling member 510 according to the preset amount of the washing liquid, thereby allowing the washing liquid with the preset amount to be added to the corresponding sample reservoir 11

An embodiment of an isolation method for isolating target particles from liquid samples is further provided according to the present disclosure. The method includes the following steps.

At step 1, the isolation chips 10 are placed on the first support platform 1, and liquid samples are placed on the second support platform 2.

At step 2, the second support platform 2 is rotated, so that the liquid samples can be moved to the second preset position 6 successively.

At step 3, the first support platform 1 is rotated, so that the isolation chips 10 can be moved to the first preset position 5 successively.

At step 4, the sampling member 510 is controlled to be rotated to form the sampling trajectory T, and the first preset position 5 and the second preset position 6 are in the sampling trajectory T. The sampling member 510 collects the liquid sample at the second preset position 6, and injects the collected liquid sample into the isolation chip 10 at the first preset position 5.

At step 5, the first chamber 16 of each isolation chip 10 is evacuated through the corresponding first outlet 161 to generate the negative pressure in the first chamber 16.

In an embodiment, before evacuating the first chamber 16, the first outlet 161 and the second outlet 181 of each isolation chip 10 are connected to the vacuum system 30. Then, the vacuum system 30 evacuates each first chamber 16 through the corresponding first outlet 161, to generate the negative pressure in each first chamber 16. Thus, compositions in each sample reservoir 11 having sizes which are smaller than sizes of the pores of the first filtration membrane 15 can enter the corresponding first chamber 16 through the corresponding first filtration membrane 15. In some cases, when the first chamber 16 has a small volume or when the negative pressure is switched too fast, the compositions having sizes which are smaller than the sizes of the pores of the first filtration membrane 15 can also enter the first liquid pool 330 through the first outlet 161.

Specifically, before evacuating, when the liquid sample is added to the sample reservoir 11 through the sample inlet 113, the sample inlet 113 can be closed. When the sample inlet 113 is closed, a flowing speed of the liquid sample in each sample reservoir 11 between the first filtration membrane 15 and the second filtration membrane 17 can be accelerated, so that the back flow adjacent to the first filtration membrane 15 and the second filtration membrane 17 can be accelerated to avoid clogging of the filtration membranes.

In other embodiments, since the plasma sample may have a large amount of proteins, at step 5, a positive pressure can also be generated in each second chamber 18 to further avoid clogging of the filtration membranes.

At step 6, vacuuming of each first chamber 16 is stopped.

At step 7, the second chamber 18 of each isolation chip 10 is evacuated through the corresponding second outlet 181 to generate the negative pressure in the second chamber 18.

When the vacuum system 30 evacuates each second chamber 18 through the corresponding second outlet 181, compositions which are absorbed on the first filtration membrane 15 may be returned to the corresponding sample reservoir 11 with the flow of air and/or liquid. Furthermore, the compositions in each sample reservoir 11 having sizes which are smaller than the sizes of the pores of the corresponding second filtration membrane 17 can enter the corresponding second chamber 18 through the corresponding second filtration membrane 17. In some cases, when the second chamber 18 has a small volume or when the negative pressure is switched to fast, the compositions having sizes which are smaller than the sizes of the pores of the corresponding second filtration membrane 17 can also enter the second liquid pool 340 through the second outlet 181. Steps 4 and 5 can also be performed simultaneously.

In other embodiments, since the plasma sample may have a large amount of proteins, at step 5, a positive pressure can be generated in each first chamber 16 to further avoid blocking and clogging of the filtration membrane.

At step 8, vacuuming of each second chamber 18 is stopped.

Then, the steps 5 to 8 can be repeated for a number of times to further remove the compositions in each liquid sample that having sizes which are smaller than the sizes of the pores of the corresponding filtration membranes, and causing the target particles having sizes which are larger than the sizes of the pores of the corresponding filtration membrane to remain in the corresponding sample reservoir 11.

In an embodiment, after step 8, the method can further include the following step.

At step 9, the washing liquid is added to the sample reservoir 11 of each isolation chip 10. Then, the step 5 to 8 can be repeated for a number of times to wash each isolation chip 10.

Using the above-described isolation device 100 to isolate and purify exosomes from a cell culture sample of 20 mL, a high yield of exosomes is obtained within 30 min.

The isolation device 100 can efficiently obtain purified exosomes from a biological sample of large volume. The advantages of the isolation device 100 include the followings of: 1) high throughput (processing multiple liquid samples, such as 2 to 100 samples, in parallel); 2) automatic processing; 3) simple and standardized operation; 4) high yield and purity; 5) free of mark; 6) cost-effective; 7) high stability and repeatability; 8) handle a variety of different biological samples, including plasma, urine, brain and marrow fluid, saliva, tears, latex, cell culture liquid, etc.

The embodiments shown and described above are only examples. Therefore, many commonly-known features and details are neither shown nor described. Even though numerous characteristics and advantages of the present technology have been set forth in the foregoing description, together with details of the structure and function of the present disclosure, the disclosure is illustrative only, and changes may be made in the detail, including in matters of shape, size, and arrangement of the parts within the principles of the present disclosure, up to and including the full extent established by the broad general meaning of the terms used in the claims. It will, therefore, be appreciated that the embodiments described above may be modified within the scope of the claims.

What is claimed is:

1. An isolation device for isolation of target particles from a plurality of liquid samples, the isolation device comprising:
a plurality of isolation chips each comprising:
a sample reservoir configured for receiving one of the plurality of liquid samples;
a first outlet and a second outlet disposed at opposite sides of the sample reservoir;
a vacuum system comprising:
a first vacuum pump connected to the first outlet of each of the plurality of isolation chips, the first vacuum pump configured to generate a negative pressure in each of the plurality of isolation chips through a corresponding first outlet; and
a second vacuum pump connected to the second outlet of each of the plurality of isolation chips, the second vacuum pump configured to generate a negative pressure in each of the plurality of isolation chips through a corresponding second outlet, to isolate the target particles from each of the plurality of liquid samples in a corresponding sample reservoir;
a first support platform adapted to rotate about a first shaft and configured to support the plurality of isolation chips, the plurality of isolation chips arranged around the first shaft and moved to a first preset position when the first support platform rotates;
a second support platform adapted to rotate about a second shaft and configured to support the plurality of liquid samples, the plurality of liquid samples arranged around the second shaft and moved to a second preset position when the second support platform rotates; and
a liquid collector comprising at least one sampling member, the at least one sampling member adapted to rotate about a third shaft to form a sampling trajectory, the first preset position and the second preset position disposed on the sampling trajectory, the at least one sampling member configured to collect one of the plurality of liquid samples at the second preset position and add the collected liquid sample to one of the plurality of isolation chips at the first preset position.

2. The isolation device of claim 1, wherein the at least one sampling member comprises two sampling members, one of the two sampling members is disposed on a side of a line connecting the first support platform and the second support platform, the other one of the two sampling members is disposed on another side of the line connecting the first support platform and the second support platform; each of the two sampling members form the sampling trajectory, respectively;
two first preset positions and two second preset positions are formed, one of the two first preset positions and a corresponding one of the two second preset positions are disposed on the sampling trajectory of one of the two sampling members, and the other one of the two first preset positions and a corresponding one of the two second preset positions are disposed on the sampling trajectory of the other one of the two sampling members.

3. The isolation device of claim 1, wherein each of the plurality of isolation chips further comprises:
a first filtration membrane comprising pores of sizes smaller than sizes of the target particles;
a second filtration membrane comprising pores of sizes smaller than the sizes of the target particles;
a first chamber connected to the sample reservoir through the first filtration membrane, the first chamber connected to the first outlet, the first chamber communicating with an ambient environment through the first outlet; and
a second chamber connected to the sample reservoir through the second filtration membrane, the second chamber connected to the second outlet, the second chamber communicating the ambient environment with the second outlet, the first chamber and the second chamber disposed at the opposite sides of the sample reservoir.

4. The isolation device of claim 1, further comprising a frequency converting module, wherein the frequency converting module is connected to the first outlet and the second outlet of each of the plurality of isolation chips through the vacuum system.

5. The isolation device of claim 4, wherein the frequency converting module comprises a frequency converter and a valve connected to the frequency converter, the valve is alternately switched to connect one of the first vacuum pump and the second vacuum pump, so that the first vacuum pump and the second vacuum pump alternately operate.

6. The isolation device of claim 3, wherein the vacuum system is configured to alternately generate the negative pressure in the first chamber and the second chamber of each of the plurality of isolation chips, which is caused by rectangular wave shaped pulse signals, periodic sinusoidal wave shaped pulse signals, or trapezoidal wave shaped pulse signals.

\* \* \* \* \*